United States Patent
Wiechers et al.

(10) Patent No.: US 9,063,114 B2
(45) Date of Patent: Jun. 23, 2015

(54) SWITCHING VALVE FOR LIQUID CHROMATOGRAPHY

(71) Applicants: Joachim Wiechers, Planegg (DE); Hermann Hochgraeber, Offenberg-Neuhausen (DE)

(72) Inventors: Joachim Wiechers, Planegg (DE); Hermann Hochgraeber, Offenberg-Neuhausen (DE)

(73) Assignee: Dionex Softron GmbH, Germering (DE)

( * ) Notice: Subject to any disclaimer, the term of this patent is extended or adjusted under 35 U.S.C. 154(b) by 136 days.

(21) Appl. No.: 13/961,594

(22) Filed: Aug. 7, 2013

(65) Prior Publication Data

US 2014/0042349 A1 Feb. 13, 2014

(30) Foreign Application Priority Data

Aug. 10, 2012 (DE) .......... 10 2012 107 377
Aug. 10, 2012 (DE) .......... 10 2012 107 378
Aug. 10, 2012 (DE) .......... 10 2012 107 379

(51) Int. Cl.
*F16K 25/00* (2006.01)
*G01N 30/26* (2006.01)
*F16K 31/04* (2006.01)
*F16K 37/00* (2006.01)
*F16K 11/074* (2006.01)
*G01N 30/20* (2006.01)

(52) U.S. Cl.
CPC .............. *G01N 30/26* (2013.01); *F16K 31/041* (2013.01); *F16K 37/0025* (2013.01); *G01N 2030/202* (2013.01); *F16K 11/0743* (2013.01); *F16K 31/043* (2013.01)

(58) Field of Classification Search
CPC ............. G01N 30/26; G01N 2030/202; F16K 11/0743; F16K 31/043; F16K 31/041; F16K 37/0025
USPC .......... 251/180, 176, 208, 209, 181, 191, 192, 251/157, 304; 137/625.17, 625.46, 625.47
See application file for complete search history.

(56) References Cited

U.S. PATENT DOCUMENTS 3,203,249 A * 8/1965 Jentzsch et al. .............. 73/23.42
3,297,053 A * 1/1967 McKinney ............... 137/625.46

(Continued)

FOREIGN PATENT DOCUMENTS

DE 438244 12/1926
DE 2934346 A1 11/1980

(Continued)

OTHER PUBLICATIONS

U.S. Appl. No. 13/979,407, filed Jul. 12, 2013.

*Primary Examiner* — Marina Tietjen
*Assistant Examiner* — Umashankar Venkatesan
(74) *Attorney, Agent, or Firm* — Timothy J. Ohara (57) ABSTRACT

A switching valve includes a stator and a rotor. The stator includes multiple connection ports. The rotor has predetermined switching positions and interacts with the stator to form a fluidic connection or a fluidic disconnection of predetermined connection ports. The rotor can be mounted rotatably via a bearing and pressing device loaded with a predefined pressing force in a direction of the stator. The bearing and pressing device includes a compensation element to load the rotor and transmit the pressing force. The compensation element is configured to make an elastic flexural deformation so that the compensation element loads the rotor when the rotor is wobbling with respect to an axis of rotation.

16 Claims, 3 Drawing Sheets

(56) References Cited

U.S. PATENT DOCUMENTS

| | | | |
|---|---|---|---|
| 3,384,118 A * | 5/1968 | Heintz et al. | 137/625.21 |
| 3,405,539 A * | 10/1968 | Tanaka | 464/87 |
| 3,542,071 A | 11/1970 | Lightner et al. | |
| 4,156,437 A * | 5/1979 | Chivens et al. | 137/554 |
| 4,390,329 A * | 6/1983 | Thorson | 418/61.3 |
| 4,444,066 A * | 4/1984 | Ogle et al. | 73/863.72 |
| 4,501,297 A | 2/1985 | Baker | |
| 6,193,213 B1 * | 2/2001 | Stearns et al. | 251/175 |
| 6,491,063 B1 | 12/2002 | Benatav | |
| 7,195,229 B2 * | 3/2007 | Maeda | 251/205 |
| 2007/0246109 A1 * | 10/2007 | Wolf et al. | 137/625.21 |
| 2010/0269936 A1 | 10/2010 | Tomita | |
| 2010/0276617 A1 | 11/2010 | Yasunaga | |
| 2010/0281959 A1 | 11/2010 | Berndt | |
| 2011/0006237 A1 | 1/2011 | Tower | |
| 2012/0061604 A1 | 3/2012 | Nowak | |

FOREIGN PATENT DOCUMENTS

| | | |
|---|---|---|
| DE | 102011000104 B4 | 2/2013 |
| EP | 0356420 A2 | 8/1989 |
| EP | 1304516 A2 | 4/2003 |
| EP | 2381124 A1 | 10/2011 |
| EP | 2165098 B1 | 4/2012 |
| GB | 2043207 A | 4/1983 |
| JP | 2009150533 | 7/2009 |
| JP | 2010531960 | 9/2010 |
| JP | 2012533041 | 12/2012 |
| WO | 9616277 A1 | 5/1996 |
| WO | 2009078450 | 6/2009 |
| WO | 2009101695 A1 | 8/2009 |
| WO | 2011008657 A2 | 1/2011 |
| WO | 2012095097 A1 | 7/2012 |

* cited by examiner

SWITCHING VALVE FOR LIQUID CHROMATOGRAPHY

CROSS-REFERENCE TO RELATED APPLICATION

This application claims the priority benefit under 35 U.S.C. §119 to German Patent Application No. 10 2012 107 377.5, filed on Aug. 10, 2012; German Patent Application No. 10 2012 107 378.3, filed on Aug. 10, 2012; and German Patent Application No. 10 2012 107 379.1, filed on Aug. 10, 2012, which are incorporated herein by reference.

FIELD OF THE INVENTION

The invention relates to a switching valve for liquid chromatography, in particular a high-pressure switching valve for high-performance liquid chromatography (HPLC).

BACKGROUND

In HPLC, high-pressure switching valves are used for an entire series of different tasks, for example in order to remove a sample to be examined from a sample container, to feed it into a sample loop and, from there, to introduce it into a high-pressure liquid flow in the direction of a chromatography column, or in order to flush various components or in order to switch over between a plurality of columns.

Switching valves of this type are installed as a rule in automatic samplers for HPLC, in column ovens or in fraction collectors.

When switching valves are used, it is almost always advantageous if only short capillary paths, that is to say short lengths of capillaries which guide the medium to be switched, are required between the relevant components. For example, when samples are guided in an eluent flow, it is advantageous if only short capillary paths have to be overcome, since the dispersion of the sample, that is to say the mixing of the sample with the eluent which is situated upstream and downstream of the sample in the flow path, is then low. In addition, the pressure loss in the relevant system is minimized by short capillary paths.

In order to make short capillary paths possible, it is advantageous or indispensable in many cases if the switching valve is constructed so as to be as compact as possible. As a result, the switching valve can be used in a space-saving and variable manner.

Despite a compact construction, it goes without saying that a switching valve of this type also has to ensure precise and reproducible positioning of the moving parts which guide the medium to be switched.

Switching valves, as used for introducing a sample into the fluid stream, normally have a stator in which there are provided multiple connection ports for the supply and discharge of the fluid to and from the switching valve. The ports are connected via ducts to opening cross sections which are formed on a switching surface of the stator, for example in the face side of a substantially cylindrical stator element. The rotor likewise has a switching surface which interacts with the switching surface of the stator, wherein in the switching surface of the rotor there are formed grooves which serve to connect certain opening cross sections and/or ports of the stator to one another as a function of two or more switching positions. Here, the rotor and the stator must be pressed against one another with an adequately high pressing force in order to attain a sealing action in the plane of the switching surfaces even in the case of high pressures such as arise in liquid chromatography, in particular HPLC.

Such switching valves are described for example in WO 2009/101695 A1 or US 2010/0281959 A1.

SUMMARY

In recent times, in HPLC, as a consequence of the high pressure used here for the medium to be switched, the stator and the rotor are configured in such a way that the two interacting faces are composed in each case of a hard material or are coated with a hard material. It is necessary in this case that the rotor is mounted such that it can wobble by sufficient angular amounts with respect to the stator, in order to compensate for production and assembly tolerances and to produce as uniform a pressure distribution as possible in the area of contact in every angular position. To this end, it is known to mount the rotor such that it can wobble by means of a flexible cushion (for example, DE 10 2011 000 104, not a prior publication; similar to WO 2011/008657 A2). This functionality is also to be capable of being realized in the valve according to the present invention.

On the basis of the prior art mentioned at the outset, the invention is therefore based on the object of providing a switching valve for liquid chromatography, in particular a high-pressure switching valve for high-performance liquid chromatography, which switching valve exhibits as homogenous a pressure distribution as possible in the contact surface between the rotor and the stator and simultaneously ensures exact guidance and positioning of the rotor and is of a compact structural size.

The invention is based on the realization that it is more favourable to produce a compensation element for making wobbling movements for the rotor possible not in the form of a cushion from a relatively soft, elastic material, such as a plastic, or to use complicated mountings, but rather to manufacture the compensation element from a relatively rigid, pressure-resistant and temperature-resistant material, in particular from a metal or ceramic, and to make the wobbling movements possible by way of a suitable geometry. This results in considerably improved temperature resistance and long-term stability.

The longitudinal axis of the compensation element (21, 21') is preferably aligned substantially with the rotational axis of the rotor (23).

According to the invention, the compensation element has a head region, which loads the rotor with a loading face, and a base region, by way of which the compensation element is supported against a unit of the bearing and pressing device, which unit generates the pressing force, or against an element of the bearing and pressing device, which element transmits the pressing force, and a bending region which is provided between the head region and the base region and is configured in such a way that it makes an elastic flexural deformation possible such that the loading face of the head region loads the full area of the rotor even in the case of wobbling movements of the rotor in every angular position of the rotor and in the process a substantially homogeneous pressure distribution is generated in the contact plane between the rotor and the stator.

In one embodiment of the invention, the head region can be of substantially rigid and flexurally strong configuration. To this end, the head region can have a cross section which is enlarged in comparison with the bending region, with the result that practically no elastic deformations take place in the head region.

A compensation element of this type can be produced in a simple way and inexpensively, for example as a simple turned part made from metal. In addition, a relatively hard, pressure-resistant material ensures excellent long-term stability.

According to one embodiment of the invention which is simple to manufacture, the compensation element is configured as a rod-shaped element or wobble bar. In particular, every hard, sufficiently pressure-resistant, sufficiently flexurally elastic and temperature-resistant material, such as steel or ceramic, is suitable as material. It goes without saying that the geometry of the compensation element also has to be selected with consideration of the material properties, in such a way that, at least in the bending region, the desired elastic deformation is ensured with maintenance of the pressure force which is to be transmitted in the axial direction.

Here, the bending region or the bending region and the base region can be configured as a preferably cylindrical region, the geometry and the material of the bending region being selected in such a way that the required wobbling movements are made possible.

According to another embodiment, the bending region can have two solid body joints or thin places which are sufficiently pressure-resistant in the axial direction in order to transmit the pressing force, the thin places or solid body joints being flexurally elastic in each case transversely with respect to the longitudinal axis of the compensation element, and the longitudinal extent planes of the two thin places, from which the bending movement takes place, or the bending axes of the solid body joints enclosing an angle which is not equal to zero, preferably lying perpendicularly on one another.

The stator of high-pressure switching valves of this type usually has a stator end face, in which a plurality of opening cross sections are formed by a plurality of ports which are formed by channels in the stator. The rotor has a rotor end face which loads the stator end face and in which one or more grooves are formed which in each case connect defined port openings in a fluidic and pressure-tight manner depending on the rotary position of the rotor with respect to the stator. In addition or instead of one or more grooves, opening cross sections of one or more connecting channels which are provided in the rotor can also be provided in the rotor end face. If the cross-sectional openings of the connecting channels are brought into congruence with the opening cross sections of predefined ports in a defined rotary position of the rotor, a connection of said ports is achieved.

The (central) region of the stator end face, in which region the opening cross sections of the ports lie, and which region has to be sealed with respect to the rotor end face (which is usually planar overall), is usually of slightly elevated configuration with respect to the surrounding region of the stator end face. The sealing area between the rotor and the stator is therefore stipulated by the size of the elevated region of the stator end face. According to one refinement of the invention, the radial extent of the loading face of the head region of the compensation element is selected to be at least as great as the radial extent of the region of the rotor end face, in which the grooves are provided. As a result, a homogeneous pressure distribution can be ensured and maintained in the contact area between the stator and the rotor. The loading face can also be selected to be as great as the entire sealing area between the rotor and the stator, which sealing area, in the case of an elevated configuration of the relevant region of the stator end face, in which region the cross-sectional openings of the ports are provided, is stipulated by said configuration.

According to one refinement of the invention, the base region of the compensation element can be supported against a coupling element of preferably cup-shaped configuration of the bearing and pressing device, the coupling element being connected to the rotor in a rotationally fixed but axially displaceable manner and so as to make required wobbling movements of the rotor possible. The coupling unit which comprises the compensation element and the coupling element rotates together with the rotor and transmits the pressing force to the rotor.

To this end, the bearing and pressing device can have a spring unit which is preferably of annular configuration and loads the coupling element with the pressing force. The coupling element can be of pot-shaped configuration, the compensation element being supported with the base region on the bottom of the coupling element and protruding beyond the end side of the coupling element with its head region, at least with the upper end face thereof which faces the rotor.

According to one refinement of the invention, the bearing and pressing device can have a receiving part which is mounted such that it can be rotated about the rotational axis of the rotor and is fixed axially, and against which the spring unit is supported, the receiving part being connected, directly or via the spring unit, fixedly to the coupling element so as to rotate with it, and the receiving part, the spring unit, the coupling element and the compensation element forming, together with the rotor, a unit which can be rotated about the rotational axis of the rotor.

Here, the receiving part can be mounted by means of a single radial bearing, preferably a radial anti-friction bearing, which has such a high axial load-bearing capability that it can absorb the axial pressing force which is necessary for pressing the rotor onto the stator. To this end, the bearing can be configured, for example, as an angular-contact ball bearing.

According to one embodiment of the invention, the receiving part can be of hollow-cylindrical or pot-shaped configuration and can have a preferably circumferential, radial flange for support with respect to the bearing, the spring unit being supported against the end side of the flange of the receiving part, which end side faces the rotor. The receiving part can therefore receive the coupling element and, if required, mount it axially displaceably and therefore centre it coaxially at the same time. However, the centering can also take place only via the spring unit which is of annular configuration and can be configured in such a way that it loads the coupling element with a radially inwardly directed centering force when the spring unit is prestressed axially (and the diameter of the annular opening is reduced as a result) from its relieved starting position (during the assembly of the valve).

On its end side (which faces the rotor) or on the flange, the receiving part can have, for example, a circumferential, axial projection which interacts, for radial positioning and fixing of the spring unit, with that region of the spring unit which is supported against the end side of the receiving part or of the flange. The spring unit can therefore be supported radially against the axial projection of the receiving part, as a result of which the spring unit itself is centered and the abovementioned centering of the coupling element can also be brought about. Since the coupling element is connected fixedly to the rotor so as to rotate with it (and it goes without saying also fixedly in the radial direction), the positioning of the rotor with respect to the stator is also brought about as a result.

According to one refinement of the invention, the receiving part has a drive region which faces away from the stator and can be coupled to the output of the drive device. As a consequence of the axial displaceability of the coupling element with respect to the receiving part and the axially fixed mounting of the receiving part, simple coupling of a drive device can therefore take place, for example in the form of an actuable motor drive or an actuating element which can be actuated manually.

BRIEF DESCRIPTION OF THE DRAWINGS

The invention will be explained in more detail below on the basis of exemplary embodiments illustrated in the drawing, in which.

DETAILED DESCRIPTION OF EMBODIMENTS

Figure 1:
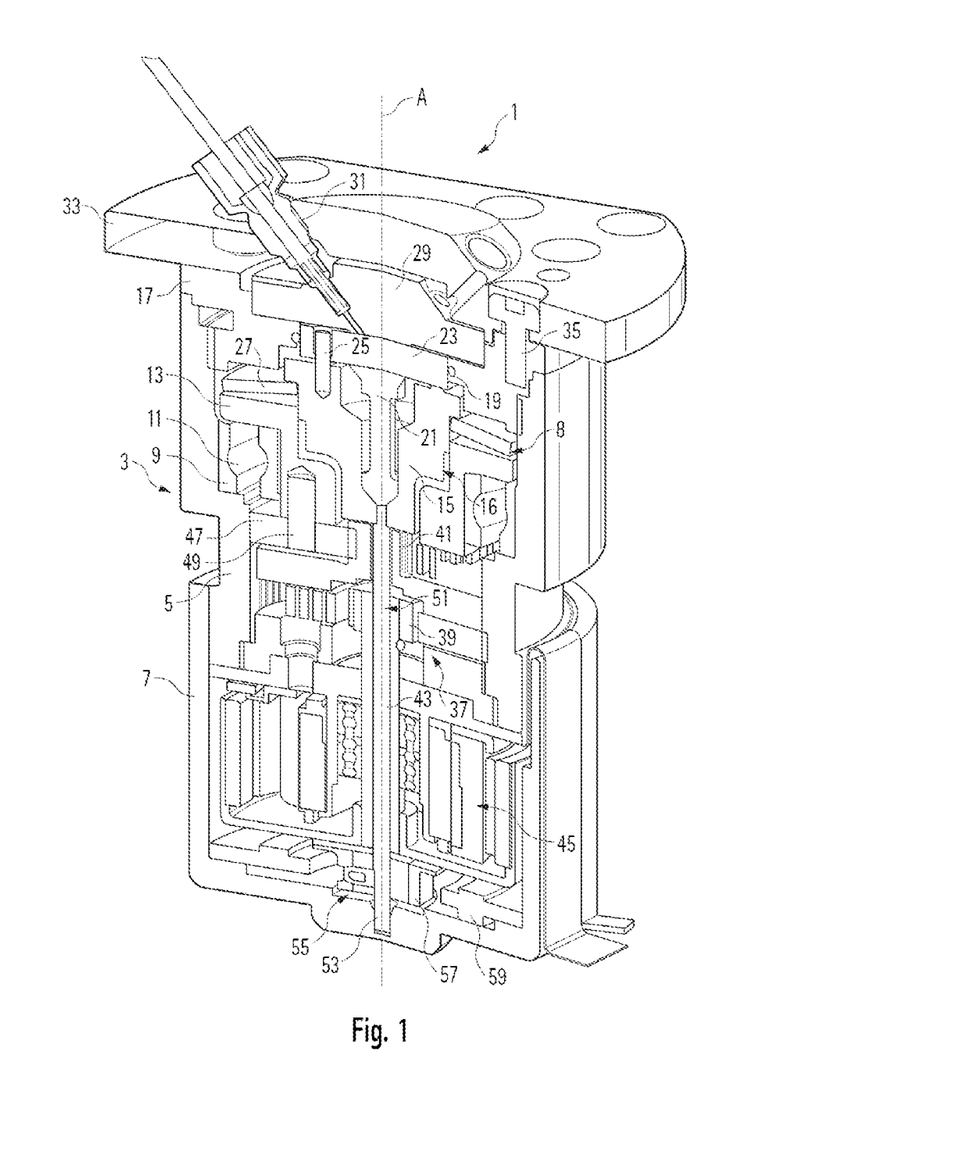
FIG. 1 is a perspective, cut-away illustration of a first embodiment of a switching valve according to the invention.

The switching valve 1 illustrated in FIG. 1 is composed of a housing 3 which has a first housing part 5 and a second housing part 7. In the second, pot-shaped, housing part 7 there is accommodated a drive unit 45, for example in the form of an electric motor. In the first housing part 5, the switching valve itself is accommodated in the upper region and a gearing unit 37 is accommodated in the lower region, which gearing unit is coupled to the drive unit 45. The first housing part 5 is closed off by means of a first cover part 17 and a second cover part 33.

The switching valve itself is composed of a stator 29, a rotor 23, and a bearing and pressing device 8 for the rotatable mounting of the rotor 23 in the housing 3 and the generation of a pressing force with which the rotor is acted on in the direction of the stator. In a known way, the stator has port opening cross sections, formed in the stator face surface, of connection ports 31 for the supply and discharge of the medium to be controlled. The stator face surface interacts with a rotor face surface of the rotor 23, in which grooves are formed. Depending on the angular position of the rotor 23 relative to the stator 29, the grooves provided in the stator end surface connect in each case predetermined port opening cross sections, such that in each case the relevant connection ports 31 are fluidically connected.

In the embodiment illustrated in FIG. 1, the bearing and pressing device 8 is composed of a bearing 11, a receiving part 13, a spring unit 27 and a coupling unit 16.

The first housing part 5 has, in its interior, a shoulder 9 on which the annular bearing 11 is supported axially. The bearing 11 is in the form of a radial bearing with adequate load-bearing capacity in the axial direction, for example an angular-contact ball bearing. The substantially hollow-cylindrical or pot-shaped receiving part 13 is supported, by way of a flange which extends radially into the housing interior almost as far as the inner wall of the housing 3 or of the housing part 5, on the bearing 11, such that the receiving part 13 is mounted so as to be fixed in the axial direction and rotationally movable. Here, the flange or the bearing 11 must self-evidently be designed such that the parts which are movable relative to one another do not come into contact, so as to permit an unhindered rotational movement. In the example illustrated, a small axial annular gap is thus provided between the outer ring of the bearing 11 and the flange of the receiving part 13.

The coupling unit 16, which is composed of a coupling element 15 and a compensation element 21, is of substantially hollow cylindrical or pot-shaped form, and extends by way of its lower region into the receiving part 13. The coupling element 15 has an outer contour which substantially corresponds to the contour of the interior of the receiving part 13. The coupling part 15 is thus guided displaceably in the axial direction by the receiving part 13.

In the embodiment of a switching valve 1 illustrated in FIG. 1, the inner diameter of the interior of the receiving part 13 is selected so as to substantially correspond to the outer diameter of the coupling element 15, such that adequately precise centering of the coupling element 15 in the radial direction relative to the receiving part 13 and thus relative to the valve axis A is attained. This is because both the stator 29, by way of its longitudinal axis (which runs perpendicular to the stator face surface and coaxially with respect to the port opening cross sections), and also the rotor 23, by way of its axis of rotation, must be aligned as precisely as possible with respect to one another such that the stator axis and the rotor axis are in alignment (and form the valve axis). At the same time, through mutually corresponding selection of the outer diameter of the coupling element 15 and of the inner diameter of the receiving part 13, precise axial displaceability of the coupling element 15 in the valve axis is attained. This however entails correspondingly low manufacturing tolerances.

In the embodiment of a switching valve 1 illustrated in FIG. 1, the coupling element 15 is rotationally conjointly connected to the receiving part 13 merely by frictional locking, and is mounted so as to be rotationally movable together therewith by means of the bearing 13. The pressing force required for the frictional locking corresponds to the pressing and/or sealing force which acts at the boundary between the rotor 23 and the stator 29 and which is generated by the spring unit 27. In the embodiment illustrated, the spring unit is realized as a single annular spring element. It is self-evidently possible for a stack of annular spring elements to be used instead of a single annular spring element.

To realize the frictional locking, the coupling element 15 has, in its upper region, a flange which extends radially outward over the circumference, which flange rests by way of its underside on the annular spring unit 27 in the form of the annular spring element 27. The spring element 27 is arranged in the annular region between the outer wall of the coupling element 15 and the inner wall of the first housing part 5, and is supported against the annular face surface of the receiving part 13 or the face surface of a radially outwardly running flange of the receiving part 13.

The rotationally conjoint connection between the coupling element 15 and the receiving part 13 may also be realized by virtue of positive locking being provided between the two parts, in particular through the formation of projections or grooves in the inner wall of the receiving part 13 and correspondingly complementary interacting grooves or projections on the outer circumference of the coupling element 15. The positive locking must however be realized such that an axial movement of the coupling element is permitted.

The rotationally conjoint connection between the coupling element 15 and the receiving part 13 may also be realized indirectly by means of positive locking between the receiving part 13 and the spring unit 27 and between the spring unit 27 and the coupling element 15.

The axial securing of the bearing and pressing device 8 in the substantially hollow cylindrical first housing part 5 is realized by means of a first cover part 17 screwed into the upper opening of the first housing part 5. The first cover part 17 is of substantially annular form and engages by way of a shoulder 19 over the upper face side of the coupling element 15, which is likewise of substantially hollow cylindrical or pot-shaped form, wherein the interior of the coupling element 15 has a tapering diameter in its lower region. The compensation element 21 in the form of a wobble bar is provided in the interior of the coupling element 15. The compensation element 21 has a substantially rigid, flexurally stiff head region, a foot region which, in the illustrated exemplary embodiment, is likewise of substantially rigid and flexurally stiff form, and a bending region provided between the foot region and head region. The compensation element 21 is supported by way of its lower end or the foot region in the interior of the coupling element 15 and projects by way of the upper end side of the head region slightly beyond the upper annular face side of the compensation element 21. As can be seen from FIG. 1, the compensation element 21 or the wobble bar is received coaxially in the coupling element 15, which in turn is received coaxially in the receiving part 13. The compensation element 21 may also be pressed by way of its foot region into the coupling part 15. In this way, precise machining of that face surface of the compensation element 21 which faces toward the stator 23 is possible in the pressed-in state. In particular, the projecting length of the face surface of the compensation element 21 in relation to the annular face surface of the coupling element 15 can be set in a precise manner by means of retroactive machining in the pressed-in state.

The rotor 23 is received in the central opening of the annular first cover part 17, wherein the outer diameter of the cylindrical rotor 23 substantially corresponds to the inner diameter of the annular cover part 17. The receiving opening however serves not for guiding the rotor 23 but rather for sealing off the interior of the housing 3 or of the housing part 5 with respect to dust, moisture and other environmental influences. For this purpose, a sealing ring may be provided in a groove formed in the inner wall of the recess, which sealing ring acts on the circumferential wall of the rotor 23 and thus provides the desired sealing action. Instead of the bores for the pins 25, the rotor 23 may also have corresponding blind holes. This yields the advantage that the bearing and pressing device 8 is sealed off with respect to the rotor face surface and, for example, no lubricant can escape to the outside from the interior of the bearing and pressing device 8.

The rotor has three axial bores which serve for receiving in each case one connecting bolt 25. The connecting bolts 25 engage by way of an upper region into the respective bore in the rotor 23 and by way of a lower end region into a corresponding bore in the face surface of the coupling element 15. In this way, the rotor is coupled rotationally conjointly to the coupling element 15. At the same time, the bores in the rotor are formed such that the rotor 23 and thus the rotor face surface are held such that they can perform a tumbling movement through a small but sufficient angular range.

The cover part 17 has, in its upper region, a receiving region for the stator 29, which is likewise of substantially cylindrical form and has multiple radially obliquely inwardly running ducts into which in each case the front end of a connection port 31 that can be screwed into a second cover part 33 extends. Of the connection ports 31, only a single connection port 31 is illustrated in FIG. 1 because the two other connection ports are situated in the respectively cut-away part of the illustration. In the same way, only a single one of the connecting bolts 25 is visible in FIG. 1. The second cover part 33 engages over the stator 29 and presses the latter by way of its stator face surface against the rotor face surface when the second cover part 33 is connected by means of screws 35 to the first cover part. The bearing and pressing device 8 and the first housing part 5 and the first and second cover parts 17, 33 are coordinated with one another here such that an adequate pressing force is generated. For the assembly of the switching valve 1, it is self-evidently also possible for the first and second cover parts 17, 33 to firstly be connected to one another, and for the cover part as a whole to then be screwed, together with the stator held therein, into the housing 3 or the first housing part 5.

For the mounting of the valve head, the bearing 11 is firstly introduced into the interior of the first housing part 5. Subsequently, the receiving part 13, the spring unit 27 and the coupling element 15 with the compensation element 21 pressed therein are inserted into the first housing part. Subsequently, the first cover part 17 is screwed on such that the above-mentioned components are fixed in the interior of the first housing part 5. Subsequently, the rotor 23 can be inserted. The cover part 17 is formed, with regard to the axial thickness of its inner region, such that the rotor 23, after the mounting onto the connecting bolt 25, still projects slightly by way of its upper face surface, in which the grooves (not illustrated in any more detail) are provided, beyond the face-side surface of the cover part 17, which supports the stator 29. Subsequently, the stator 29 is placed onto the rotor 23 such that the lower face side of the stator, in which the opening cross sections of the ducts connected to the connection ports 31 are provided, rests on the upper face surface of the stator 23. It must be taken into consideration here that the central region of the stator face surface in which the opening cross sections of the ports are situated, and which must be sealed off with respect to the rotor face surface (which is normally, on the whole, planar), is normally formed so as to be raised slightly in relation to the surrounding region of the stator face surface. The sealing surface between the rotor and stator is thus defined by the size of the raised region of the stator face surface.

The second cover part 33 is subsequently placed on, which second cover part is designed so as to act on the upper side of the stator 29. The second cover part 33 is connected to the first cover part 17 by means of the screws 35, whereby the stator 29 is acted on with an axial force such that an axially acting sealing force is generated which is sufficient to seal off the grooves provided in the rotor 23 with respect to the stator face surface or the central, raised region of the stator face surface even at the high pressures prevailing in the HPLC. The pressure force is generated here by the spring unit 27 in the form of the annular spring element and/or by the screwing-on of the second cover part 33.

As already described above, the compensation element 21 in the illustrated embodiment has an adequately rigid head region and an adequately rigid foot region which are not deformed, or are at most scarcely (elastically) deformed, under the pressing force to be transmitted from the coupling element 15 to the rotor 23. By contrast, the interposed cylindrical bending region permits an elastic bending deformation such that the upper face surface, by which the compensation element 21 acts on that surface of the rotor 23 which faces towards it, can jointly perform possible wobbling movements of the rotor, and here, the contact pressure at the contact surface between the upper face surface of the compensation element 21 and the rotor 23 is substantially uniformly distributed. Furthermore, the compensation element 21 acts on the rotor 23 coaxially, such that, in the likewise coaxial pressing surface between the rotor 23 and the stator 29, a substantially uniform pressure distribution is attained even if the rotor 23 performs a wobbling movement about its axis during a rotation because the stator face surface and/or the rotor face surface do not run exactly perpendicular to the axis of rotation of the rotor 23.

Here, the bending region of the compensation element 21 must self-evidently also be sufficiently pressure-resistant that the desired pressing force can be transmitted to the rotor 23.

Said region must thus be designed to be at least as rigid as the spring unit 27 in the axial direction. It is only adequate bending elasticity that is desired.

It is pointed out at this juncture that the foot region of the compensation element 21 need not imperatively be of flexurally stiff form. Said foot region may be in the form of an elongation of the bending region, such that the bending region and foot region are combined to form one region with identical or very similar characteristics. A rigid foot region however facilitates the coaxial support with respect to the element which transmits the pressing force, in this case the coupling element 15. Furthermore, a rigid, flexurally stiff foot region can facilitate the pressing of the compensation element 21 into the coupling element 15.

In another embodiment which is not illustrated, it is also possible to dispense with a specially designed head region, wherein the bending region and head region may have the same cross section.

Figure 2:
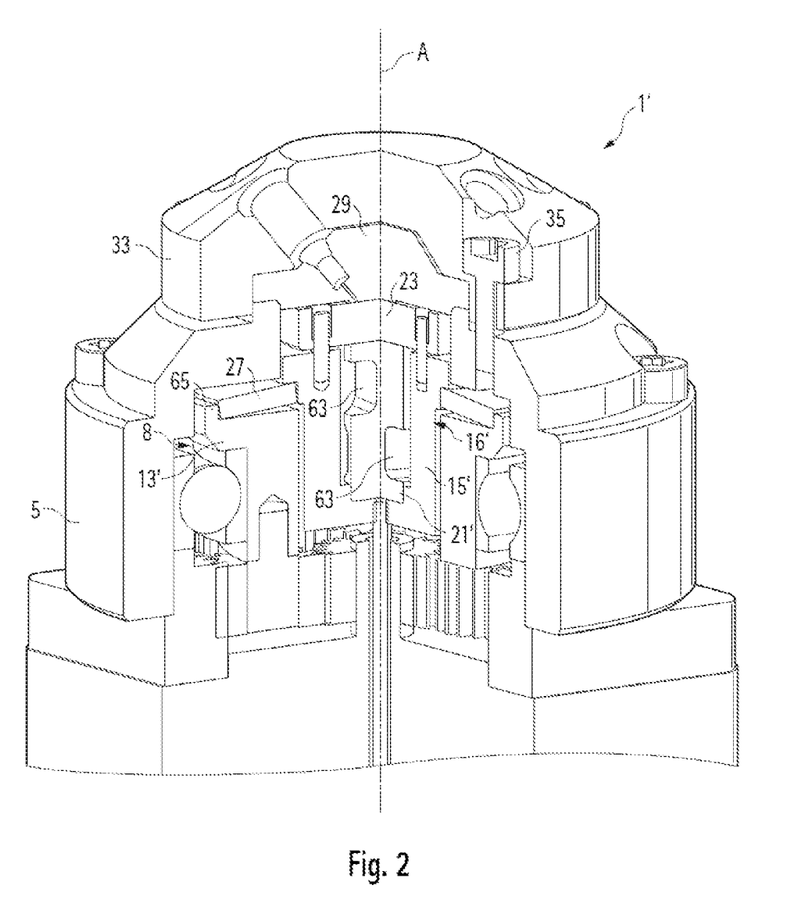
FIG. 2 is a perspective, cut-away illustration of the switching valve itself (without drive device) of a second embodiment of a switching valve according to the invention.

In the embodiment illustrated in FIG. 2 of a valve 1' according to the invention, substantially only the upper part is illustrated, that is to say the valve itself which is accommodated in the first housing part 5.

Said embodiment substantially equates to the embodiment in FIG. 1 and differs substantially only in two crucial aspects.

Firstly, the compensation element 21' is designed differently. Secondly, the centering of the coupling element 16' is realized no longer by means of an axially displaceable and radially fixed mounting of the coupling element 15' in the receiving part 13.

Instead of a cylindrical bending region with a relatively small diameter, the compensation element 21' has two bending regions, offset with respect to one another by 90° about the longitudinal axis, in the form of constrictions 63. In the embodiment illustrated in FIG. 2, the constrictions have a constant thickness and run parallel and symmetrically with respect to the longitudinal axis of the compensation element 21'. The constrictions 63 may however also be of any other form suitable for ensuring respectively adequate bending elasticity in the direction perpendicular to the surface of the constriction or to the longitudinal plane of extent thereof (in the case of a symmetrical embodiment of the plane of symmetry). It is also possible for the axial length of the constrictions 63 to be reduced to such an extent that they are practically in the form of solid joints with corresponding pivot axes running perpendicular to one another.

The compensation element 21' designed in this way thus also permits a wobbling movement of the rotor 23 and simultaneously transmits the required axial pressing force to the rotor 23.

For the centering of the coupling unit 16', the outer diameter of the coupling element 15' is selected to be slightly smaller than the inner diameter of the interior of the receiving part 13, such that at least pre-centering of the coupling element 15' and thus also of the coupling element 16' and of the rotor 23 in the radial direction relative to the receiving part 13 is generated.

The annular spring element 27, which again is in the form of a plate spring, is supported by way of its outer circumference in the radial direction against an encircling axial edge 65 of the radially extending flange of the receiving part 13'. By way of its inner surface of the annular chamber, the spring unit 27 acts on the outer circumference of the coupling element 15', wherein the diameter of the respective region of the coupling element 15' even in the unloaded state substantially corresponds to the inner diameter of the spring unit 27. During the assembly of the switching valve 1', the spring unit 27 is compressed axially such that the inner diameter is reduced and the spring unit 27 acts on the coupling element 15' with a radially inwardly directed force and in this way effects the centering of the coupling unit 16'.

The mode of operation of the switching valve 1' otherwise corresponds to the mode of operation of the switching valve 1 illustrated in FIG. 1, such that in this regard, reference is made to the statements made above.

The following description applies to both variants of switching valves 1, 1' as per FIGS. 1 and 2, wherein the description is given only with reference to FIG. 1, and can be transferred analogously to the embodiment as per FIG. 2.

In the embodiment illustrated in FIG. 1, in the lower region of the first housing part 5, there is provided a planetary gear set which, in the exemplary embodiment illustrated, has two transmission ratio stages. The gearing unit in the form of the planetary gear set therefore has two sun gears 39, 41 which have in each case a hollow axle. A hollow cylindrical drive output shaft 43 of a drive unit 45 is inserted into the hollow axle of the sun gear 39. The sun gear 39 is connected rotationally conjointly to the drive output shaft 43. The drive unit 45 and the gearing unit 37 together form the drive device for the rotational movement of the rotor 23 of the switching valve 1.

Of three planet gears or planet wheels 47 of the second stage of the planetary gear set, only one planet wheel 47 is visible in FIG. 1. Each planet wheel 47 has a coaxial pen 49 which engages into a corresponding receiving bore in the lower face side of the wall of the receiving part 13. In this way, each of the planet wheels 47 and thus the entire drive output of the planetary gear set, is connected to the receiving part 13, such that the receiving part 13 can hereby be driven in rotation.

A transmission element 51 in the form of a bar-shaped element 53 is guided through the hollow cylindrical drive output shaft 43 of the drive unit 45 and through the sun gear 41. The bar-shaped element engages by way of its upper end into the lower receiving opening of the coupling element 15 and is connected rotationally conjointly to the coupling element 15, for example by adhesive bonding, welding or the like.

As can be seen from FIG. 1, the bar-shaped element 53 engages through the drive device formed by the gearing unit 37 and the drive unit 45, and is supported by way of its lower end in a receptacle in the base of the second housing part 7.

Here, the bar-shaped element 53 jointly performs every rotational movement of the rotor 23, wherein the rotational movement is loaded at most by frictional forces and otherwise takes place in a load-free manner. As a result, there are practically no torsional forces whatsoever within the bar-shaped element, such that the rotational position of the lower end of the bar-shaped element 53 constitutes an exact reproduction of the rotational position of the rotor 23.

It is pointed out at this juncture that said exact reproduction is subject at most to a degree of play that arises as a result of the connection of the rotor 23 to the coupling element 15 via the connecting bolts 25. This is because the receiving bores in the rotor 23 must be slightly larger than the outer diameter of the connecting bolts 25 in order to permit a slight wobbling movement of the rotor 23. This is necessary in order to compensate manufacturing and/or assembly tolerances which result in the face surface of the rotor 23 and the face surface of the stator 29 not being positioned exactly in alignment. Said wobbling movements are made possible by the fact that the rotor 23 rests by way of its lower face surface on the face surface of the compensation element or the wobble bar 21. The latter is dimensioned such that it can be deformed within the required narrow limits by the high axial forces that must be transmitted via the compensation element 21 from the coupling element 15 to the rotor 23.

By contrast, as already stated, the rotational movement of the bar-shaped element 53 takes place in a substantially load-free manner.

In the lower region, that is to say in the rear region of the drive unit 45, there is provided a device 55 for detecting the rotational position of the rotor. Said device comprises a marker element 57 which is connected, in the lower region, to the bar-shaped element 53. For this purpose, the marker element 57 may have a central bore through which the bar-shaped element 53 extends. The fixing may be realized for example by means of adhesive bonding or by means of a knurled screw. Furthermore, the device for detecting the rotational position of the rotor comprises a sensor element 59 which is arranged so as to be situated opposite the circumferential surface of the substantially cylindrical marker element 57. The marker element may for example have magnetic or optical marks or markings along its circumferential surface, the movement or position of which marks or markings is detected by the sensor element 59. The signal of the sensor element 59 may be supplied to an evaluation and control unit (not illustrated in any more detail). The latter can actuate the drive unit 45, as a function of the signal from the device for detecting the rotational position of the rotor 23, such that the rotor 23 is moved in a controlled manner into a predefined rotational position.

The marker element 57 and the sensor element 59 may for example be designed such that magnetic or optical position detection takes place. A suitable sensor element 59 is for example a Hall sensor for detecting magnetic marks of a corresponding magnetic marker element 57. As an optical detector or optical sensor element 59, use may be made, for example, of a photodiode which detects light reflected by the optical marks of the respective optical marker element 57. For this purpose, the optical marks of the marker element 57 may for example also be illuminated by an LED.

In principle, however, any device for detecting the rotational position of the rotor is suitable which is capable of detecting the circumferential position or circumferential movement of the transmission element 51 in the form of the bar-shaped element 53 and generating a corresponding signal.

As a result of the provision of corresponding marks on the marker element 57, it is possible here to determine both the absolute rotational position and also the relative rotational position in relation to a predefined initial value.

In an embodiment which is not illustrated, the device 55 for detecting the rotational position of the rotor may also be designed such that the transmission element 51 or the bar-shaped element 53 actuate a potentiometer, preferably the sliding contact of a potentiometer. Even though, in this embodiment, the position detection does not take place in a contactless manner, it can be realized in an extremely simple and inexpensive form.

Figure 3:
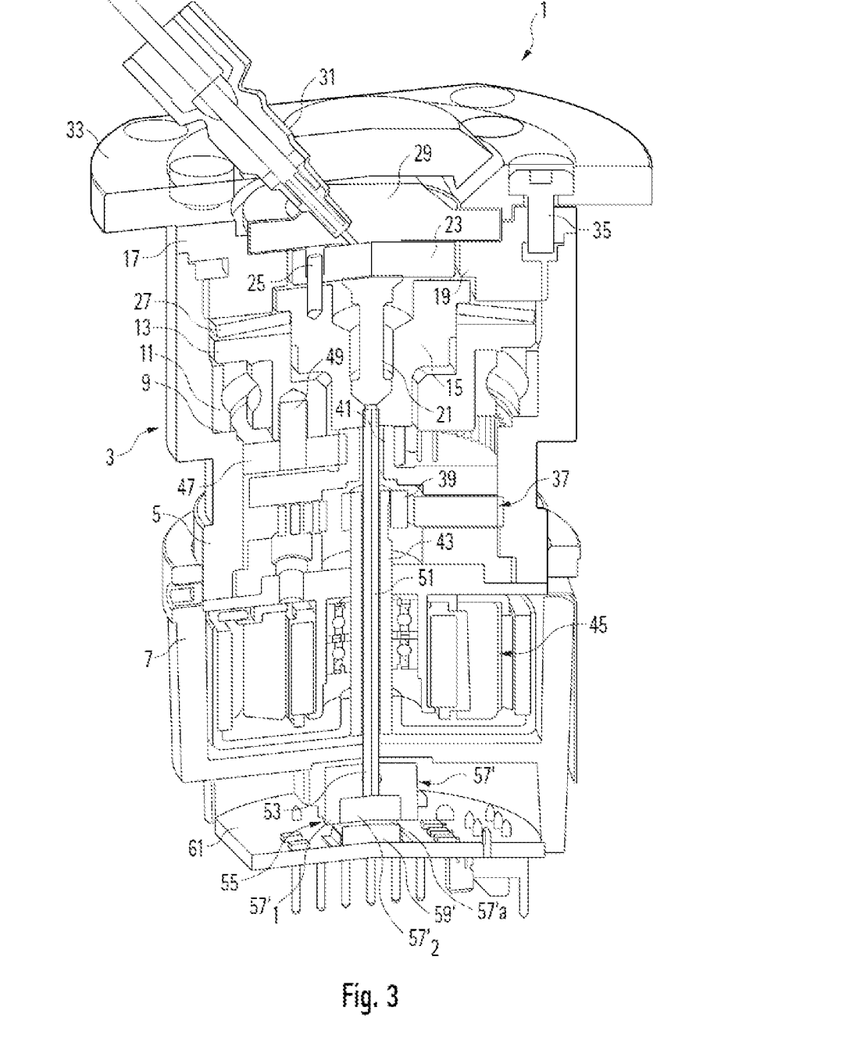
FIG. 3 is a perspective, cut-away illustration of a further embodiment of a switching valve according to the invention.

The embodiment of a switching valve 1 illustrated in FIG. 3 differs from the embodiment as per FIG. 1 substantially merely in that the device for detecting the rotational position of the rotor is arranged not radially at the lower end of the bar-shaped element 53 but rather axially. For this purpose, the device 53 comprises a marker element 57' which, in turn, has a coaxial bore into which the lower end of the bar-shaped element 53 engages. In the case of this marker element 57', however, the marker surface itself or the markings are provided not on the radially outwardly pointing circumferential surface, as is the case in the embodiment as per FIG. 1, but rather on the downwardly directed face surface 57'a thereof.

As illustrated in FIG. 2, the marker element 57' may also be formed in two parts and have a receiving part $57_1$ which, on the face side, has a pot-shaped recess in which the marker element itself, for example a radially magnetized permanent magnet $57'_2$, is arranged and held.

The retention and guidance of the bar-shaped element 53 is realized in the exemplary embodiment illustrated in FIG. 3 merely by the fastening to the coupling element 15 and by means of the engagement through the drive output shaft 43 and through the sun gears 39 and 41. The mounting and guidance of the bar-shaped element 52 may however also be realized additionally or exclusively in the housing part 7.

Opposite the face surface 57'a of the marker element 57' there is arranged a sensor element 59' in the form of a Hall sensor chip which is capable of detecting the magnetic marker (radially running) of the radially magnetized permanent magnet $57'_2$. The sensor element 59' is provided on a printed circuit board 61 on which are also provided the electronics for the evaluation and generation of a signal which represents the absolute or relative position of the rotor 23.

Since the device 55 or the evaluation electronics is situated at the axially rear end region of the switching valve 1, it is possible in all of the embodiments as per FIGS. 1 to 3 for the switching valve to be inserted by way of its front head region (for example including the entire first housing part 5) into a wall of a column oven. Owing to the position of the device 55, the sensor device and/or corresponding evaluation electronics are prevented from being exposed to inadmissibly high temperatures.

It is pointed out here that it is self-evidently also possible in the embodiment as per FIG. 1 for evaluation electronics or detection electronics for generating a suitable analogue or digital signal, which represents the position of the rotor in the form of a digital or analogue signal, to be provided in the lower base region of the second housing part 7.

Furthermore, said structural form has the advantage that the device for detecting the rotational position of the rotor is provided axially in the rear region, and a highly compact structural form can be attained overall. In particular, the structural form is not increased with regard to its radial extent by the provision of a corresponding device 55. This makes it possible for multiple such switching valves 1 to be positioned, for example inserted into the wall of a column oven, with a very small spacing between their axes.

What is claimed is:

1. A switching valve comprising:
   (a) a stator arranged in a housing, the stator including multiple connection ports;
   (b) a rotor configured to be rotated, is arranged in the housing and, in which the rotor has predetermined switching positions and interacts with the stator to form a fluidic connection or a fluidic disconnection of predetermined connection ports;
   (c) the rotor being mounted rotatably via a bearing and pressing device, where the bearing and pressing device is arranged in the housing and loaded with a predefined pressing force in a direction of the stator;
   (d) in which the bearing and pressing device includes a compensation element to load the rotor and transmit the pressing force; and
   (e) the compensation element includes a head region, a base region, and a bending region, the head region loads the rotor with a loading face, the base region is supported against a coupling unit of the bearing and pressing device to generate the pressing force or against a coupling element of the bearing and pressing device to generate the pressing force, the bending region disposed between the head region and the base region, and configured to make an elastic flexural deformation so that the head region loads the rotor when the rotor is wobbling with respect to an axis of rotation.

2. The switching valve of claim 1, in which a substantially homogeneous pressure distribution is generated in a contact plane between the rotor and the stator while wobbling.

3. The switching valve of claim 1, in which the head region is substantially rigid and has a cross section that is larger than a cross section of the bending region.

4. The switching valve of claim 1, in which the compensation element is a rod-shaped element.

5. The switching valve of claim 1, in which the bending region is cylindrical.

6. The switching valve of claim 1, in which the bending region includes two constrictions, the two constrictions configured to transmit the pressing force and to be flexurally elastic transversely with respect to a longitudinal axis of the compensation element, and longitudinal extent planes of the two constrictions, from which the bending movement takes place, enclosing an angle which is not equal to zero.

7. The switching valve of claim 6, in which the angle is a perpendicular angle.

8. The switching valve of claim 1, in which the stator includes a stator end face, the connection ports have a port opening cross section at the stator end face, the rotor includes a rotor end face, the rotor end face including one or more grooves, in which the switching valve has a predetermined switching position where one of the grooves connects predetermined port opening cross sections in a pressure-tight manner, and in that the radial extent of the loading face of the head region of the compensation element is configured to be at least as great as a radial extent of a region of the rotor end face in which the grooves are formed.

9. The switching valve of claim 1, in which the base region of the compensation element is supported against a coupling element, the coupling element having a cup-shaped configuration.

10. The switching valve of claim 9, in which the bearing and pressing device further includes a spring unit having an annular configuration, the spring unit configured to load the coupling element with the pressing force.

11. The switching valve of claim 10, in which the bearing and pressing device further includes a receiving part coupled to the rotor and configured to be rotated about the rotational axis of the rotor, the receiving part supporting the spring unit and fixed axially to the spring unit, the receiving part being connected to the coupling element and fixedly connected to the spring unit, where the receiving part, the spring unit, the coupling element, the compensation element, and the rotor are all be rotated about the rotational axis of the rotor.

12. The switching valve of claim 11, in which the receiving part is mounted with a radial bearing.

13. The switching valve of claim 12, in which the receiving part includes a hollow-cylindrical configuration, and a circumferential radial flange to support the receiving part on the radial bearing, the spring unit being supported against an end side of the flange.

14. The switching valve of claim 13, in which the receiving part further includes a circumferential axial projection configured to radially position and fix the spring unit to the end side of the flange.

15. The switching valve of claim 11, in which the receiving part has a drive region facing away from the stator and coupled to the output of a drive device.

16. The switching valve of claim 15, in which the output of the drive device is coupled to the drive region of the receiving part.

\* \* \* \* \*